United States Patent
Jones et al.

(10) Patent No.: US 9,683,953 B2
(45) Date of Patent: Jun. 20, 2017

(54) XRF ANALYZER COMMUNICATION

(71) Applicant: Moxtek, Inc., Orem, UT (US)

(72) Inventors: Vincent Floyd Jones, Cedar Hills, UT (US); Daniel N. Paas, Spanish Fork, UT (US); Brad Harris, Farmington, UT (US); Bill Hansen, Manteca, CA (US)

(73) Assignee: Moxtek, Inc., Orem, UT (US)

( * ) Notice: Subject to any disclaimer, the term of this patent is extended or adjusted under 35 U.S.C. 154(b) by 196 days.

(21) Appl. No.: 14/821,350

(22) Filed: Aug. 7, 2015

(65) Prior Publication Data

US 2016/0054242 A1   Feb. 25, 2016

Related U.S. Application Data

(60) Provisional application No. 62/039,767, filed on Aug. 20, 2014.

(51) Int. Cl.
*G01N 23/223* (2006.01)
*G08C 17/02* (2006.01)

(52) U.S. Cl.
CPC ........... *G01N 23/223* (2013.01); *G08C 17/02* (2013.01)

(58) Field of Classification Search
CPC ........... G01N 23/223; G01N 2223/076; G01N 2223/301; G08C 17/02
USPC ...................................................... 378/43–50
See application file for complete search history.

(56) References Cited

U.S. PATENT DOCUMENTS

| | | | |
|---|---|---|---|
| 7,889,335 B2 * | 2/2011 | Durst ....................... | G01J 3/02 356/326 |
| 7,933,379 B2 | 4/2011 | Grodzins et al. | |
| 8,155,268 B2 | 4/2012 | Pesce et al. | |
| 8,355,126 B2 | 1/2013 | Goulter et al. | |
| 8,494,113 B2 | 7/2013 | Grodzins | |
| 2007/0174152 A1 * | 7/2007 | Bjornberg .............. | G01C 15/00 705/28 |

FOREIGN PATENT DOCUMENTS

EP   2389865 A1   11/2011

* cited by examiner

*Primary Examiner* — Courtney Thomas
(74) *Attorney, Agent, or Firm* — Thorpe, North & Western, LLP

(57) ABSTRACT

An x-ray fluorescence (XRF) analysis system 10 can include an XRF analyzer 20 which can communicate wirelessly with other devices. The system 10 can also include remote-processor software configured to be loaded onto a handheld electronic device 23 and/or remote-computer software configured to be loaded onto a remote-computer 28. The XRF analyzer 20 can include a microphone 18 and/or an output device 31 to allow a user 19 to communicate conveniently with the XRF analyzer 20.

9 Claims, 1 Drawing Sheet

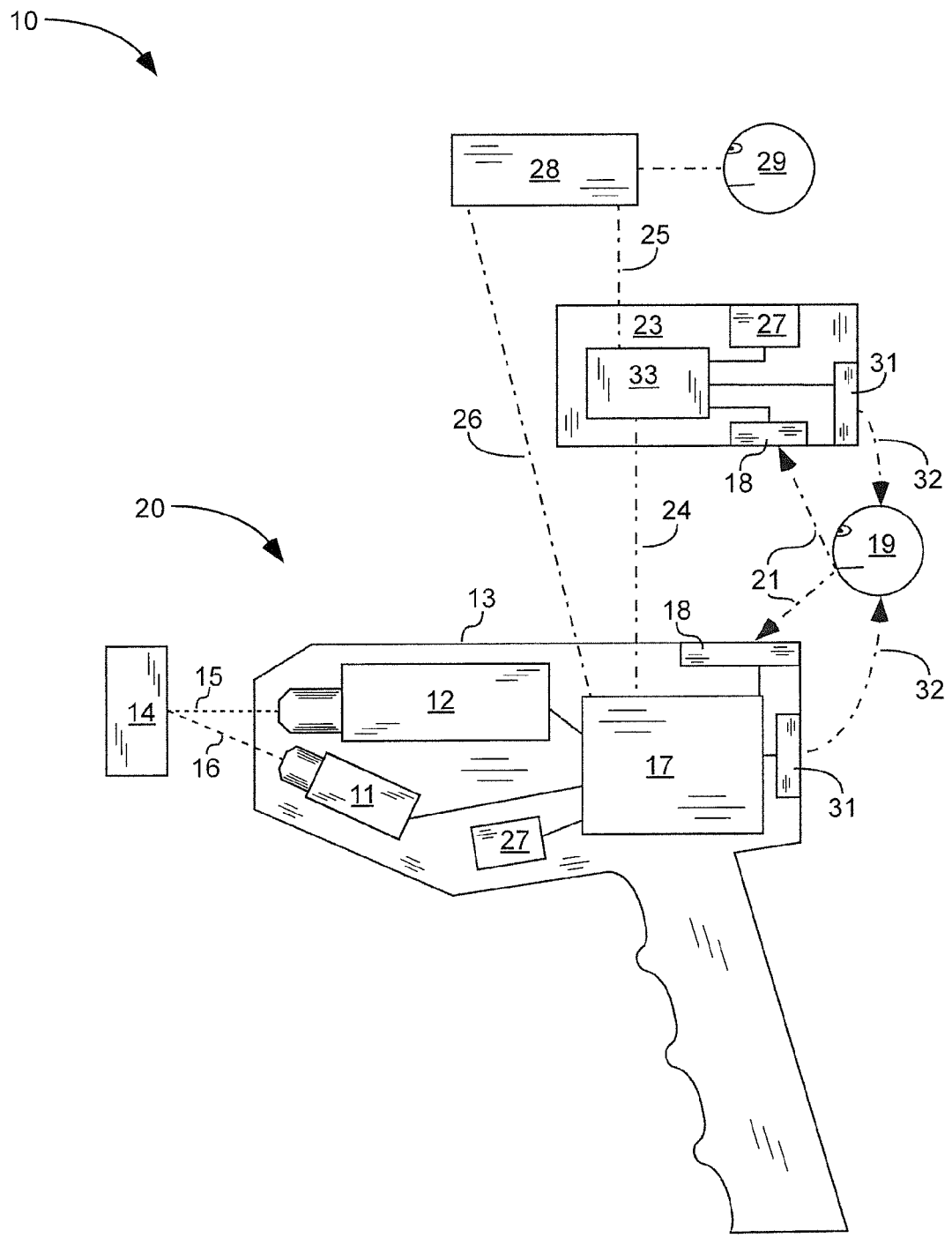

XRF ANALYZER COMMUNICATION

CLAIM OF PRIORITY

This claims priority to U.S. Provisional Patent Application No. 62/039,767, filed on Aug. 20, 2014, which is hereby incorporated herein by reference in its entirety.

FIELD OF THE INVENTION

The present application is related generally to x-ray fluorescence analyzers.

BACKGROUND

X-ray fluorescence (XRF) analyzers are used for material analysis. Handheld XRF analyzers are useful due to their convenience. XRF analyzers are often used in chemical manufacturing, inspection for hazardous materials such as lead or cadmium, metal manufacturing, and metal sorting.

A goal of improving XRF analyzers is cost reduction. Another goal of improving XRF analyzers is to maintain its functionality and avoid shutdown of an operation due to XRF analyzer failure.

One goal of improving handheld XRF analyzers is weight and size reduction in order to avoid operator fatigue. Avoiding loss, theft, and improper use, especially of a handheld XRF analyzer, are also important. Increasing battery life is another goal for improving handheld XRF analyzers. XRF analyzer durability is another desirable feature.

It can be difficult for a user of an XRF analyzer, especially a handheld XRF analyzer, to place and hold the XRF analyzer in the correct position for analysis while selecting an analysis program. Improved user convenience would be beneficial to XRF analyzer users.

XRF analyzers can be programmed for various uses, such as to analyze for various, different elements or to determine if a material is compatible with certain governmental or manufacturing standards. Fast and convenient updating of available XRF analyzer programs would be beneficial to users.

Some or all of the above description may also be applicable to laser-induced breakdown spectroscopy (LIBS) analysis tools, x-ray diffraction (XRD) analysis, and Raman spectroscopy tools.

SUMMARY

It has been recognized that it would be advantageous to reduce x-ray fluorescence (XRF) analyzer cost, maintain XRF analyzer functionality, reduce XRF analyzer weight and size, avoid XRF analyzer loss, avoid XRF analyzer theft, avoid XRF analyzer improper usage, improve XRF analyzer user convenience, increase battery life, increase XRF analyzer durability, and increase speed and convenience in updating XRF analyzer programs. The present invention is directed to various embodiments of XRF analyzers or XRF analysis systems that satisfy these needs. Each embodiment can satisfy one, some, or all of these needs.

The XRF analyzer can include an x-ray source and an x-ray detector disposed in a housing. The x-ray source can be disposed in a location and oriented to emit x-rays towards a sample and the x-ray detector can be disposed in a location and oriented to receive fluoresced x-rays emitted from the sample. At least a portion of an electronic-processor can be attached to the housing.

In one embodiment, a microphone can be attached to the XRF analyzer. The microphone can be configured to receive a verbal command from a user of the XRF analyzer and to send an initial signal, based on the verbal command. The electronic-processor can be configured to select or obtain a program based on the initial signal. The electronic-processor can be configured to operate the XRF analyzer based on the program selected.

In another embodiment, an output device can be attached to the XRF analyzer. The output device can be configured to give to a user notification of: acknowledgement of a program selected by the user, XRF analysis results, a countdown until XRF analysis begins, a countdown until XRF analysis ends, instructions on proper use of the XRF analyzer, and/or a notification of analysis completion.

An XRF analysis system can include the XRF analyzer and remote-processor software configured to be loaded onto a handheld electronic device, to cause wireless communication between the handheld electronic device and the XRF analyzer.

BRIEF DESCRIPTION OF THE DRAWINGS

FIG. 1 is a schematic view of an XRF analysis system 10 including a schematic cross-sectional side view of an XRF analyzer 20, in accordance with an embodiment of the present invention.

DEFINITIONS

As used herein, the term "handheld electronic device" includes tablets, phablets, smart phones, and other devices that have both long-range and short-range wireless communication ability and can easily be held in one hand. As used herein, the term "handheld electronic device" does not include laptop computers.

As used herein, the term "handheld XRF analyzer" means an XRF analyzer that is designed to be held by a single hand of a user. For example, a handheld XRF analyzer can have a weight of around four pounds.

As used herein, the terms "long-range wireless" and "short-range wireless" are relative to each other. Presently, "short-range wireless" refers to devices that can communicate wirelessly with other devices over a range of up to about 100 meters. Also, with present technology, "long-range wireless" refers to devices that can communicate wirelessly with other devices over a range of more than 100 meters, even up to around 30,000 meters. These distances are only representative of present technology and may change as wireless technology improves. Short-range wireless devices are typically less expensive, smaller, and lighter than long-range wireless devices, so cost saving may be obtained by using only short-range wireless technology on an XRF analyzer and using a long-range wireless device as a bridge between the XRF analyzer and a remote-computer.

As used herein, the term "software" includes computer software and apps for devices such as smart phones and tablets.

DETAILED DESCRIPTION

XRF Analyzer

As illustrated in FIG. 1, an x-ray fluorescence (XRF) analysis system 10 is shown including an XRF analyzer 20. The XRF analyzer can include an x-ray source 12 and an x-ray detector 11 attached to or disposed in a housing 13. The x-ray source 12 can be located and oriented to emit x-rays 15 towards a sample 14. The x-ray detector 11 can be located and oriented to receive fluoresced x-rays 16 emitted from the sample 14. An electronic-processor 17 can be attached to the housing 13. The XRF analyzer 20 can be handheld. "Attached to" means a direct attachment to the housing or to the housing via intermediate structures.

Handheld Electronic Device and Remote-Computer

Shown in FIG. 1 is a handheld electronic device 23 and a remote-computer 28. The XRF analysis system 10 can include remote-processor software for the handheld electronic device 23 and/or remote-computer software for the remote-computer 28. In a typical use of the XRF analysis system 10, the XRF analyzer 20 and the handheld electronic device 23 will both be held by or attached to a user 19 and the remote-computer 28 will be far away—perhaps at least five thousand meters away or even on an opposite side of the world.

The handheld electronic device 23 can be physically separate from and independently movable from the XRF analyzer 20. A remote-processor 33 can be attached to the handheld electronic device 23 and can control, or at least partially control the handheld electronic device 23. The remote-processor software can be loaded onto the remote-processor 33 and can be configured to cause the handheld electronic device 23 to wirelessly send information to and receive information from the electronic-processor 17 and/or the remote computer 28. The electronic-processor 17 can cause the XRF analyzer 20 to wirelessly send information to and receive information from the handheld electronic device 23 and/or the remote computer 28. Alternatively, a cable, such as a USB cable for example, can be used to transmit information between the electronic-processor 17 and the remote-processor 33.

The remote-computer 28 can be physically separate from and independently movable from the XRF analyzer 20 and the handheld electronic device 23. The remote-computer software can be loaded onto the remote-computer 28 and can be configured to cause the remote-computer 28 to wirelessly send information to and receive information from the electronic-processor 17 and/or the remote computer 28. Information can be wirelessly transmitted directly between the XRF analyzer 20 and the remote computer 28, or through the handheld electronic device 23.

The handheld electronic device 23 can be held by or attached to the body of the user 19 (e.g. on a belt or in a pocket). The XRF analyzer 20 would then only need short-range wireless capability to communicate to the remote-computer 28 via the handheld electronic device 23. This can reduce the cost, size, and weight of the XRF analyzer because devices for long-range wireless communication tend to be more expensive, larger, and heavier than devices for short-range wireless communication.

The handheld electronic device 23 can be a smart phone which many people already have and which is already being used for other purposes. Thus, there might be no added cost for the handheld electronic device 23. Such handheld electronic devices 23 can already equipped to communicate long-range to the remote-computer 28, such as through a cell phone tower, a satellite, or an area WyFi to the Internet. For wireless device cost saving, the electronic-processor 17 can be configured to transmit and receive wirelessly the information 24 over a short-range, such as for example a maximum distance of 10 meters in one aspect or over a maximum distance of 100 meters in another aspect.

Another benefit of using the handheld electronic device 23 is that the user can utilize a screen of the handheld electronic device 23 as a touch pad for entering instructions or as a display to show analysis results. Thus, the XRF analyzer 20 can be made at a lower cost, weight, and size by not needing a display screen. This can also increase XRF analyzer durability as display screens can be delicate. Use of the display screen on the handheld electronic device 23 instead of a display screen on the XRF analyzer 20 can also extend the XRF analyzer 20 battery life.

Microphone, Program Selection & Updates, and Remote Processing,

A microphone 18 can be attached to the housing 13 and/or to the handheld electronic device 23. The microphone 18 can be electrically connected to the electronic-processor 17 or to the remote-processor 33. If used, the handheld electronic device 23 might already be equipped with a microphone 18, and thus there would be no added cost for this device. Use of a microphone 18 on the handheld electronic device 23 instead of a microphone 18 on the XRF analyzer 20 can extend the XRF analyzer 20 battery life. On the other hand, it might be more convenient for the user to speak into a microphone 18 on the XRF analyzer.

The microphone 18 can be configured to receive a verbal command 21 from a user 19 and to transmit an initial signal, based on the verbal command 21, to the electronic-processor 17 or to the remote-processor 33. The verbal command 21 can be a command to begin the analysis based on a specific program. For example, the user could say "steel analysis" and a program would be selected and analysis performed as described above to determine the type of steel.

The microphone 18 can increase convenience of a user 19 of the XRF analyzer 20. Without the microphone 18, the user 19 may need to hold the XRF analyzer 20 with one hand and type in the desired program with the other hand. This can be inconvenient and time consuming. The microphone 18 can increase convenience and speed of analysis and can allow the user 19 to use the XRF analyzer 20 with one hand. Use of the microphone 18 can also allow the user to focus on holding the XRF analyzer in the proper position, which can be difficult if the user needs to type instructions into the unit.

The initial signal can be received by the electronic-processor 17 directly from the microphone 18 or wirelessly from the remote-processor 33. The electronic-processor 17 can select a program based on the initial signal. The program can be selected from a library of programs stored on the electronic-processor 17.

Alternatively, the electronic-processor 17 can obtain the program from the remote-processor 33 or from the remote computer 28. For example, the remote-processor 33 can receive the initial signal directly from the microphone 18 or from the electronic-processor, then select or obtain the program based on the initial signal. The program can then be wirelessly transmitted from the remote-processor 33 to the electronic-processor 17.

The remote-processor 33 can select the program from a library of programs stored on the remote-processor 33. Alternatively, the remote-processor 33 can wirelessly transmit the initial signal to the remote-computer 28. The remote-computer 28 can then select the program from a library of programs stored on the remote-computer 28. The remote-computer can then wirelessly transmit the program to the electronic-processor 17 directly or to the remote-processor 33.

In the above examples, it is possible that the initial signal changes in form as it is transmitted from one device to another, but it is still called an initial signal.

The program can include x-ray source 12 voltage, x-ray source 12 flux intensity, x-ray source 12 flux duration, x-ray source 12 filter setting, x-ray detector 11 filter setting, and/or other commands. The electronic-processor 17 can be configured to operate the XRF analyzer 20 based on the program selected. The electronic-processor 17 can then operate the XRF analyzer 20 based on instructions in the program.

The electronic-processor 17 or the remote-processor 33 can periodically communicate with the remote-computer 28 for updates to the library, such as new programs/software or updates to existing programs.

Having the remote-computer 28 or the remote-processor 33 store programs and send instructions to the XRF analyzer 20 to carry out the analysis can allow for a smaller, lighter, and less expensive electronic-processor 17 on the XRF analyzer. Having the remote-computer 28 provide updates to a library of programs on the electronic-processor 17 or on the remote-processor 33 can allow the user 19 to have convenient and rapid access to the most updated programs available. Having the remote-computer 28 provide updates to a library of programs on the electronic-processor 17 or on the remote-processor 33 can allow the XRF analyzer 20 seller to sell individual programs easily. These programs can be apps that can be downloaded onto the handheld electronic device 23. Also, this can be a theft deterrent because a thief might not have access to any of the programs or updates to the programs.

Output Device

An output device 31 can be attached to the housing 13 of the XRF analyzer 20 and electrically connected to and controlled by the electronic-processor 17. An output device 31 can be attached to the handheld electronic device 23 and electrically connected to the remote-processor 33. The output device 31 on the handheld electronic device 23 can be controlled by the remote-processor software. The output device 31 can be configured to give notification 32 to the user 19 of information related to use of the XRF analyzer 20. For example, the output device 31 can notify 32 the user 19 of:

1. an acknowledgement of the program selected, e.g. RoHS or lead analysis;
2. XRF analysis results, e.g. whether or not cadmium is present or type of steel;
3. instructions on proper use of the XRF analyzer 20, e.g. hold the analyzer steady;
4. a countdown until XRF analysis begins;
5. a countdown until XRF analysis ends;
6. and/or a notification of analysis completion.

The notification 32 to the user 19 can be various forms of communication, such as for example:

1. A verbal notification 32. Thus the output device 31 can be a speaker which can verbally tell the user 19 the information. A verbal notification 32 can be helpful if more complicated information needs to be conveyed, such as for example percent of chromium in steel. A verbal notification 32 can be helpful if the user 19 needs to reach to do the analysis and it would be difficult for the user 19 to see an output screen. A verbal notification can be helpful due to its speed and simplicity.
2. A light or multiple lights. For example, a green light can indicate successful pass of analysis (e.g. no lead) and a red light for failure (e.g. lead is present). A light can indicate successful receipt of a command. The light can remain on or can blink at a certain frequency to provide the notification 32 to the user 19.
3. A vibrator. For example, vibration can indicate passing an analysis or successful receipt of a command. On/off vibration at a certain frequency can provide more complicated notification 32.
4. A movable mechanical device, such as for example a movable mechanical plunger that can be felt by the user. This may be beneficial if the user 19 is in a heavy duty industrial environment.

The various output devices can be beneficial for convenient and rapid analysis.

If used, the handheld electronic device 23 might already be equipped with an output device 31, and thus there would be no added cost for this device. Use of an output device 31 on the handheld electronic device 23 instead of an output device 31 on the XRF analyzer 20 can extend the XRF analyzer 20 battery life. On the other hand, it might be more convenient for the user to receive input from an output device 31 on the XRF analyzer or the handheld electronic device 23 might not have the desired type of output device 31.

XRF Analyzer Global Position

A global positioning system (GPS) device 27 can be attached to the XRF analyzer 20, and can be electrically connected to the electronic-processor 17. The GPS device 27 can be attached to the handheld electronic device 23 and electrically connected to the remote-processor 33; and can be controlled by the remote-processor software on the remote-processor 33.

The GPS device 27 can be configured to transmit a location signal, indicating a global position of the XRF analyzer 20 and/or the handheld electronic device 23, to the electronic-processor 17 or to the remote-processor 33. The electronic-processor 17 can be configured to wirelessly transmit 26 the location signal directly from the electronic-processor 17 to the remote-computer 28. The electronic-processor 17 can be configured to wirelessly transmit 24 the location signal to the remote-processor 33, then the remote-processor 33 can be configured to wirelessly transmit 25 the location signal to the remote-computer 28. If the GPS device 27 is on the handheld electronic device 23, then the remote-processor 33 can be configured to wirelessly transmit 25 the location signal to the remote-computer 28. The location signal can be useful for locating a lost or stolen XRF analyzer 20.

The handheld electronic device 23 might already be equipped with a GPS device 27, and thus there would be no added cost for this device. Also, use of a GPS device 27 on the handheld electronic device 23 instead of on the XRF analyzer 20 can extend the XRF analyzer 20 battery life. As the handheld electronic device 23 and the XRF analyzer 20 may be used together, location of one device can indicate a global position of the other device. It may be preferred, however, to have the GPS device 27 on the XRF analyzer 20 if it is likely that only the XRF analyzer 20 without the handheld electronic device 23 is lost or stolen.

The remote-computer software and the remote-processor software can cause the remote-computer and the remote-processor 33, respectively, to function as just described.

Remote Disable

Sometimes it can be beneficial to the XRF analyzer 20 supplier or user 19 to have the ability to remotely disable the XRF analyzer 20. The supplier might desire to remotely disable the XRF analyzer 20 if the XRF analyzer 20 was under lease, then the user 19 failed to return the XRF analyzer 20 at the end of the lease. The supplier or user 19 might desire to remotely disable the XRF analyzer 20 if the XRF analyzer 20 is stolen.

The XRF analysis system 10 can be configured to allow the remote-computer 28 to wirelessly transmit 26 a disable signal directly to the XRF analyzer 20. Alternatively, the XRF analysis system 10 can be configured to allow the remote-computer 28 to wirelessly transmit 25 the disable signal from the remote-computer 28 to the remote-processor 33, then wirelessly transmit 24 the disable signal from the remote-processor 33 to the electronic-processor 17. Upon receipt of the disable signal, the electronic-processor 17 can be configured to prevent operation of the XRF analyzer 20. The remote-computer software and the remote-processor software can cause the remote-computer and the remote-processor 33, respectively, to function as just described.

Remote Analysis and Monitoring

The electronic-processor 17 can be configured to monitor XRF analyzer 20 performance and usage and create an analysis signal based on this monitored information. The analysis signal can be wirelessly transmitted 26 from the electronic-processor 17 to the remote-computer 28 directly. The analysis signal can be wirelessly transmitted 24 from the electronic-processor 17 to the remote-processor 33, then optionally from the remote-processor 33 to the remote-computer 28.

The remote-computer 28 or the remote-processor 33 can analyze the analysis signal and can wirelessly transmit (26, 24, or 24 plus 25) or by other means provide a response to the user 19 or to a remote operator 29. For example, if the analysis signal indicates that the XRF analyzer 20 is approaching failure, then the remote-computer 28 can instruct the user 19 to send in the unit for repair or can instruct the remote operator 29 to mail a replacement XRF analyzer to the user 19 before the presently used XRF analyzer 20 fails, and thus avoid downtime. Based on the analysis signal, the remote-computer 28 can provide information to the remote operator 29 for improvement of future XRF analyzers.

The monitored information can be x-ray source 12 filament resistance or x-ray detector 11 cooling time. An increase in filament resistance or x-ray detector 11 cooling time can indicate that the XRF analyzer 20 is approaching failure. The monitored information can be hours of usage, x-ray tube voltage, number of analysis performed, and number of charges to a battery of a handheld XRF analyzer.

The remote-computer software and the remote-processor software can cause the remote-computer and the remote-processor 33, repetively, to function as just described.

XRF, XRD, LIBS, and Raman

Some or all of the above description, and the following claims, may also be applicable to laser-induced breakdown spectroscopy (LIBS), x-ray diffraction (XRD) analyzers, and Raman spectroscopy tools. The term "XRF analyzer" used herein can be replaced by some or all of the following: LIBS spectrometer, XRD analyzer, Raman spectroscopy equipment, and XRF analyzer.

What is claimed is:

1. An x-ray fluorescence (XRF) analyzer, comprising:
   a. a housing;
   b. an x-ray source and an x-ray detector attached to the housing, wherein:
      i. the x-ray source is located and oriented to emit x-rays towards a sample; and
      ii. the x-ray detector is located and oriented to receive fluoresced x-rays emitted from the sample;
   c. a microphone and an electronic-processor attached to the housing, wherein:
      i. the microphone is configured to receive a verbal command from a user and to transmit an initial signal, based on the verbal command, to the electronic-processor;
      ii. the electronic-processor is configured to select or obtain a program based on the initial signal;
      iii. the electronic-processor is configured to operate the XRF analyzer based on the program selected;
   d. the electronic-processor is configured to wirelessly-transmit the initial signal to a remote-processor attached to a handheld electronic device;
   e. the handheld electronic device is physically separate from and independently movable from the XRF analyzer;
   f. the electronic-processor is configured to receive a wirelessly-transmitted return signal from the remote-processor, the return signal including a program, selected by the remote-processor, and based on the initial signal;
   g. the electronic-processor is configured to operate the XRF analyzer based on the program.

2. The XRF analyzer of claim 1, wherein the XRF analyzer forms part of an XRF analysis system, the XRF analysis system further comprising the remote-processor, the remote-processor configured to:
   a. wirelessly receive the initial signal;
   b. select the program from a library of programs stored on the remote-processor; and
   c. wirelessly transmit the return signal.

3. The XRF analysis system of claim 2, further comprising a remote-computer that is physically separate from and independently movable from the XRF analyzer and the handheld electronic device, and wherein:
   a. the remote-processor is configured to communicate wirelessly with the remote-computer;
   b. the remote-computer is configured to communicate wirelessly with the remote-processor; and
   c. the remote processor is configured to receive a signal transmitted wirelessly from the remote-computer to modify the library.

4. The XRF analyzer of claim 1, further comprising a global positioning system (GPS) device attached to the housing, wherein:
   i. the GPS device is configured to transmit a location signal to the electronic-processor;
   ii. the electronic-processor is configured to wirelessly transmit the location signal to a remote-computer; and
   iii. the location signal indicates a global position of the XRF analyzer.

5. The XRF analyer of claim 1, wherein
the electronic-processor is configured to receive a disable signal from a remote-computer and upon receipt of the disable signal to prevent operation of the XRF analyzer.

6. The XRF analyzer of claim 1, wherein:
the electronic-processor is configured to monitor XRF analyzer performance, XRF analyzer usage, or both and to generate an analysis signal based on the monitored XRF analyzer performance, XRF analyzer usage, or both;
the electronic-processor is configured to wirelessly transmit the analysis signal to a remote-computer.

7. The XRF analyzer of claim 6, further comprising
the remote-processor
and
the electronic-processor is configured to wirelessly-transmit the analysis signal to the remote-processor.

8. The XRF analyzer of claim 6, wherein monitoring XRF analyzer performance includes monitoring:
   a. filament resistance;
   b. x-ray detector cooling time;
   c. number of analysis performed;
   d. hours of usage;

e. x-ray tube voltage;
f. number of charges to a battery; or
g. combinations thereof.

9. The XRF analyzer of claim 1, further comprising an output device attached to the housing and electrically connected to the electronic-processor, the output device configured to give notification by vibration, an indicator light, verbal communication, a movable mechanical device, or combinations thereof to the user of:
   a. an acknowledgement of the program selected by the user;
   b. XRF analysis results;
   c. instructions on proper use of the XRF analyzer;
   d. a countdown until XRF analysis begins;
   e. a countdown until XRF analysis ends;
   f. a notification of analysis completion; or
   g. combinations thereof.

* * * * *